US009243381B2

(12) United States Patent
Behmlander et al.

(10) Patent No.: US 9,243,381 B2
(45) Date of Patent: Jan. 26, 2016

(54) EROSION MONITORING SYSTEM FOR GROUND ENGAGING TOOL

(71) Applicant: Caterpillar Inc., Peoria, IL (US)

(72) Inventors: Matthew J. Behmlander, Metamora, IL (US); Terri L. Atkinson, Farmington, IL (US); Jeremy R. Hammar, Germantown Hills, IL (US); Robert L. Meyer, Metamora, IL (US)

(73) Assignee: Caterpillar Inc., Peoria, IL (US)

( * ) Notice: Subject to any disclaimer, the term of this patent is extended or adjusted under 35 U.S.C. 154(b) by 165 days.

(21) Appl. No.: 13/866,394

(22) Filed: Apr. 19, 2013

(65) Prior Publication Data

US 2014/0311762 A1 Oct. 23, 2014

(51) Int. Cl.
*E02F 3/815* (2006.01)
*E02F 3/76* (2006.01)
*E02F 9/26* (2006.01)
*E02F 9/28* (2006.01)
*G01N 29/07* (2006.01)

(52) U.S. Cl.
CPC .............. *E02F 3/8152* (2013.01); *E02F 3/7604* (2013.01); *E02F 3/765* (2013.01); *E02F 3/7645* (2013.01); *E02F 3/7654* (2013.01); *E02F 9/267* (2013.01); *E02F 9/2808* (2013.01); *E02F 9/2875* (2013.01); *G01N 29/07* (2013.01); *G01N 2291/02854* (2013.01); *G01N 2291/044* (2013.01)

(58) Field of Classification Search
USPC ................. 172/719, 772, 772.5, 430; 37/446, 37/450–454, 460; 175/39
See application file for complete search history.

(56) References Cited

U.S. PATENT DOCUMENTS

| | | | | |
|---|---|---|---|---|
| 2,468,905 A | * | 5/1949 | Warren, Jr. | 175/39 |
| 2,549,278 A | * | 4/1951 | Yancey | 175/39 |
| 4,922,423 A | * | 5/1990 | Koomey et al. | 702/39 |
| 5,033,031 A | * | 7/1991 | Bohman | 367/96 |
| 5,743,031 A | * | 4/1998 | Launder et al. | 37/455 |
| 5,777,231 A | * | 7/1998 | Patel et al. | 73/660 |
| 6,868,711 B2 | | 3/2005 | Ebi | |
| 7,014,271 B2 | | 3/2006 | Burger et al. | |

(Continued)

FOREIGN PATENT DOCUMENTS

| | | |
|---|---|---|
| KR | 101087961 | 12/2011 |
| WO | 2006116758 | 11/2006 |
| WO | 2010117331 | 10/2010 |

OTHER PUBLICATIONS

Instruction Guide for Using the Massa M3 Wireless Ultrasonic Tank Level Sensor Evaluation Kit. Massa. Oct. 20, 2011.*

(Continued)

*Primary Examiner* — Matthew D Troutman
(74) *Attorney, Agent, or Firm* — Finnegan, Henderson, Farabow, Garrett & Dunner, LLP

(57) ABSTRACT

An erosion monitoring system is disclosed for use with a machine. The erosion monitoring system may have an ultrasonic sensor embedded within a replaceable cutting edge of a ground engaging tool connectable to the machine. The erosion monitoring system may also have a wireless communication element associated with the ultrasonic sensor, and a controller mountable onboard the machine in communication with the ultrasonic sensor via the wireless communication element. The controller may be configured to monitor a wear rate of the cutting edge based on signals from the ultrasonic sensor.

13 Claims, 2 Drawing Sheets

(56) References Cited

U.S. PATENT DOCUMENTS

| | | | |
|---|---|---|---|
| 7,631,560 B2* | 12/2009 | Lund et al. | 73/629 |
| 7,908,928 B2 | 3/2011 | Vik et al. | |
| 7,954,380 B2* | 6/2011 | Lund et al. | 73/629 |
| 2002/0194916 A1* | 12/2002 | Yamada et al. | 73/627 |
| 2006/0044146 A1 | 3/2006 | Ferguson et al. | |
| 2006/0243839 A9 | 11/2006 | Barscevicius et al. | |
| 2007/0044447 A1 | 3/2007 | Viaud | |
| 2007/0088523 A1 | 4/2007 | Keller | |
| 2007/0256862 A1* | 11/2007 | Lund et al. | 175/39 |
| 2008/0153402 A1* | 6/2008 | Arcona et al. | 451/352 |
| 2009/0297273 A1 | 12/2009 | Lindbergh et al. | |
| 2009/0313860 A1 | 12/2009 | Breiner et al. | |
| 2011/0046857 A1 | 2/2011 | Farmer et al. | |
| 2012/0043980 A1 | 2/2012 | Davies | |
| 2012/0256470 A1* | 10/2012 | Von Schoenebeck et al. | 299/10 |
| 2013/0068027 A1* | 3/2013 | Sullivan et al. | 73/628 |

OTHER PUBLICATIONS

EPO, International Search Report, PCT/US2006/016518, filing date Oct. 30, 2006.

EPO, International Search Report, PCT/US2012/057831, filing date Sep. 28, 2012.

De Broissia, M., et al., "Global Optimisation of Disc Cutter Tool Life for Tunnel Boring Machine Preparing 4th Eurothen Workshop," Bouygues Travaux Publics.

Zhang, Z.X., et al., Measurements of cutter forces and cutter temperature of boring machine in Aspo Hard Rock Laboratory, Tech. Rpt TR-01-34, Apr. 2001.

Shanahan, A., Cutter Instrumentation System for Tunnel Boring Machines, The Robbins Co., Kent, WA, available Sep. 17, 2010.

McKinley, Timothy Allen, et al., "Sensor System and Method" U.S. Appl. No. 13/628,662, filed Sep. 27, 2012.

* cited by examiner

EROSION MONITORING SYSTEM FOR GROUND ENGAGING TOOL

TECHNICAL FIELD

The present disclosure relates generally to an erosion monitoring system and, more particularly, to an erosion monitoring system for a ground engaging tool.

BACKGROUND

Machines, for example motor graders, dozers, wheel loaders, and excavators are commonly used in material moving applications. These machines include a ground engaging tool having a cutting edge configured to contact the material. During use of the cutting edge, the material abrades the cutting edge, causing it to erode away. Accordingly, the cutting edge is sometimes removably attached to the tool and replaced on a periodic basis. Alternatively, the entire ground engaging tool is replaced on a periodic basis.

The cutting edge or the tool itself is replaced when it is determined that it has eroded beyond an acceptable limit. To make this determination, a service technician is typically called out to the machine and measures a length of the cutting edge using a measuring tape. The measured length is then compared to the acceptable limit, and selectively replaced based on the comparison. This process of determining when to replace the cutting edge and/or tool can be labor intensive and inaccurate.

An alternative way to measure erosion of a tool is described in U.S. Patent Publication 2006/0243839 of Barscevicius et al. that published on Nov. 2, 2006 ("the '839 publication"). Specifically, the '839 publication discloses using an imbedded sensor to measure erosion of wearing parts of a crusher. The sensor is comprised of a network of resistors that wear away from the network, as the sensor is worn along with the erosion of the wearing parts being monitored. With the erosion of the wearing parts (and the resistors), the overall resistance of the sensor changes. Signals associated with the changing resistance are then delivered to a crusher setting control system for use in setting control parameters of the crusher.

Although the wear sensor of the '839 publication may offer a way to monitor erosion of a wear part, it may be less than optimal. In particular, the sensor may require the resistors to be embedded within the wear parts during fabrication of the wear parts. In some applications, the fabrication process may be too harsh for the resistors and cause the sensor to fail. In addition, the sensor is damaged during use of the crusher, thereby inhibiting the sensor from being reused. Further, the network of resistors may require significant power be supplied to the sensor. This large amount of power may require a hard-wired connection to the sensor, which may inhibit use of the sensor in some applications. Further, the signals generated by the network of resistors may change in a step-wise manner as individual resistors are removed from the network, thereby limiting accuracy in the signals generated by the sensor.

The erosion monitoring system of the present disclosure addresses one or more of the needs set forth above and/or other problems of the prior art.

SUMMARY

In one aspect, the present disclosure is directed to an erosion monitoring system for use with a machine. The erosion monitoring system may include an ultrasonic sensor embedded within a replaceable cutting edge of a ground engaging tool connectable to the machine. The erosion monitoring system may also include a wireless communication element associated with the ultrasonic sensor, and a controller mountable onboard the mobile machine in communication with the ultrasonic sensor via the wireless communication element. The controller may be configured to monitor a wear rate of the cutting edge based on signals from the ultrasonic sensor.

In another aspect, the present disclosure is directed to a ground engaging tool. The ground engaging tool may include a base member, and a cutting edge removably connected to the base member. The cutting edge may have a bore formed therein, and the ground engaging tool may further include an ultrasonic sensor disposed within the bore. The ultrasonic sensor may be configured to generate a signal indicative of a length of the cutting edge.

DETAILED DESCRIPTION

Figure 1:
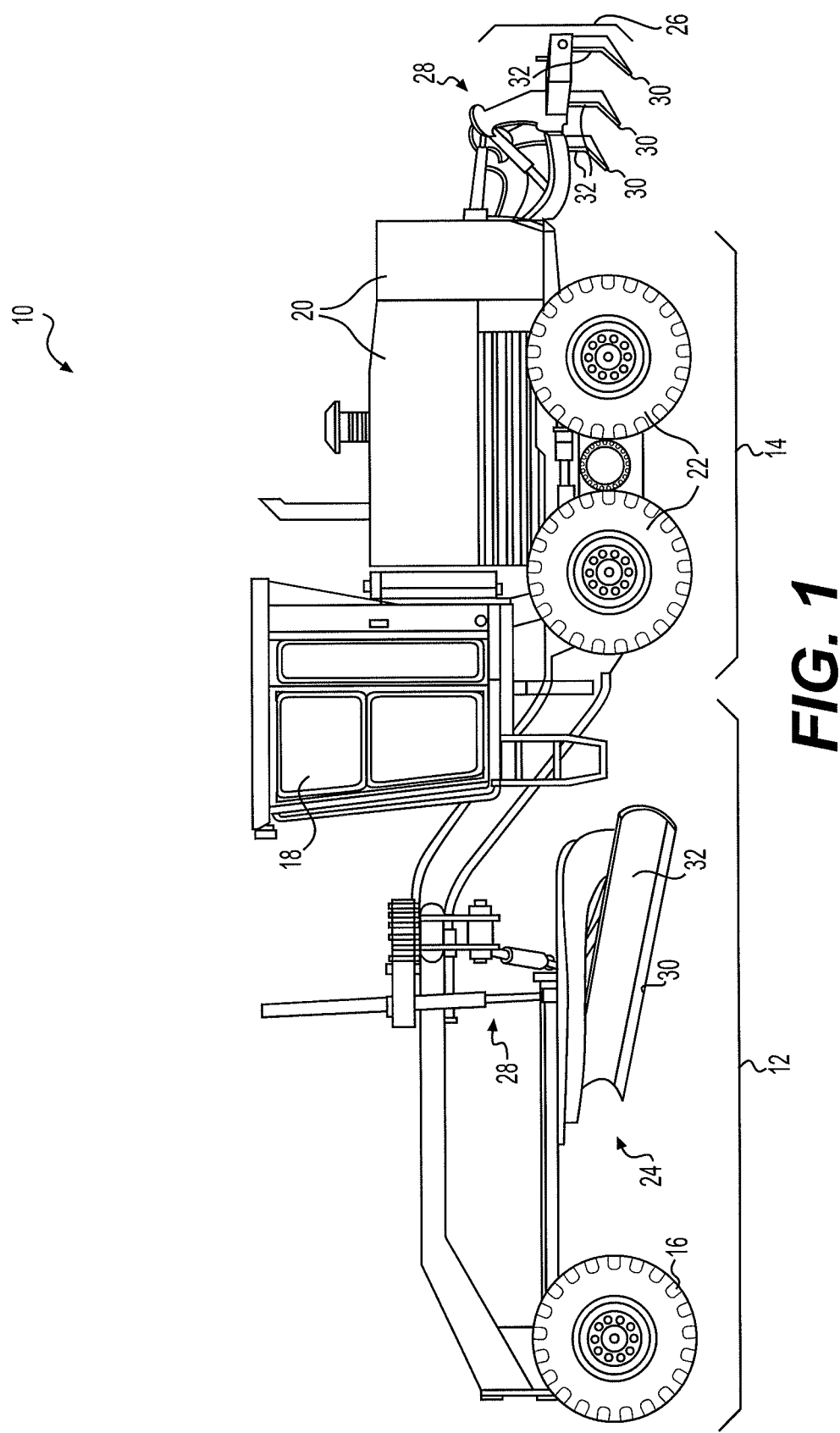
FIG. 1 is an isometric illustration of an exemplary disclosed machine.

An exemplary embodiment of a machine 10 is illustrated in FIG. 1. Machine 10 may be, for example, a motor grader, a backhoe loader, an agricultural tractor, a wheel loader, a skid-steer loader, a dozer, an excavator, or any other type of machine known in the art. As a motor grader, machine 10 may include a steerable front frame 12 and a driven rear frame 14 that is pivotally connected to front frame 12. Front frame 12 may include a pair of front wheels 16 (or other traction devices), and support an operator station 18. Rear frame 14 may include compartments 20 for housing a power source (e.g., an engine) and associated cooling components, the power source being operatively coupled to rear wheels 22 (or other traction devices) for primary propulsion of machine 10. Wheels 22 may be arranged in tandems on opposing sides of rear frame 14. Steering of machine 10 may be a function of both front wheel steering and articulation of front frame 12 relative to rear frame 14.

Machine 10 may also include one or more ground engaging tools such as, for example, a drawbar-circle-moldboard (DCM) 24 that is operatively connected to and supported by front frame 12, and a ripper assembly 26 that is operatively connected to and supported by rear frame 14. It is contemplated that DCM 24 and/or ripper assembly 26 may be connected to and supported by another portion of machine 10, if desired, such as by another portion of front frame 12 and/or rear frame 14. Both of DCM 24 and ripper assembly 26 may be supported via separate hydraulic ram arrangements 28. Hydraulic ram arrangements 28 may be configured to shift DCM 24 and ripper assembly 26 vertically toward and away from front frame 12, shift DCM 24 and ripper assembly 26 side-to-side, and/or rotate DCM 24 and ripper assembly 26 about a horizontal or vertical axis. It is contemplated that DCM 24 and ripper assembly 26 may move in additional and/or different ways than described above, if desired. It is also contemplated that additional, different, and/or fewer ground engaging tools may be connected to machine 10.

Figure 2:
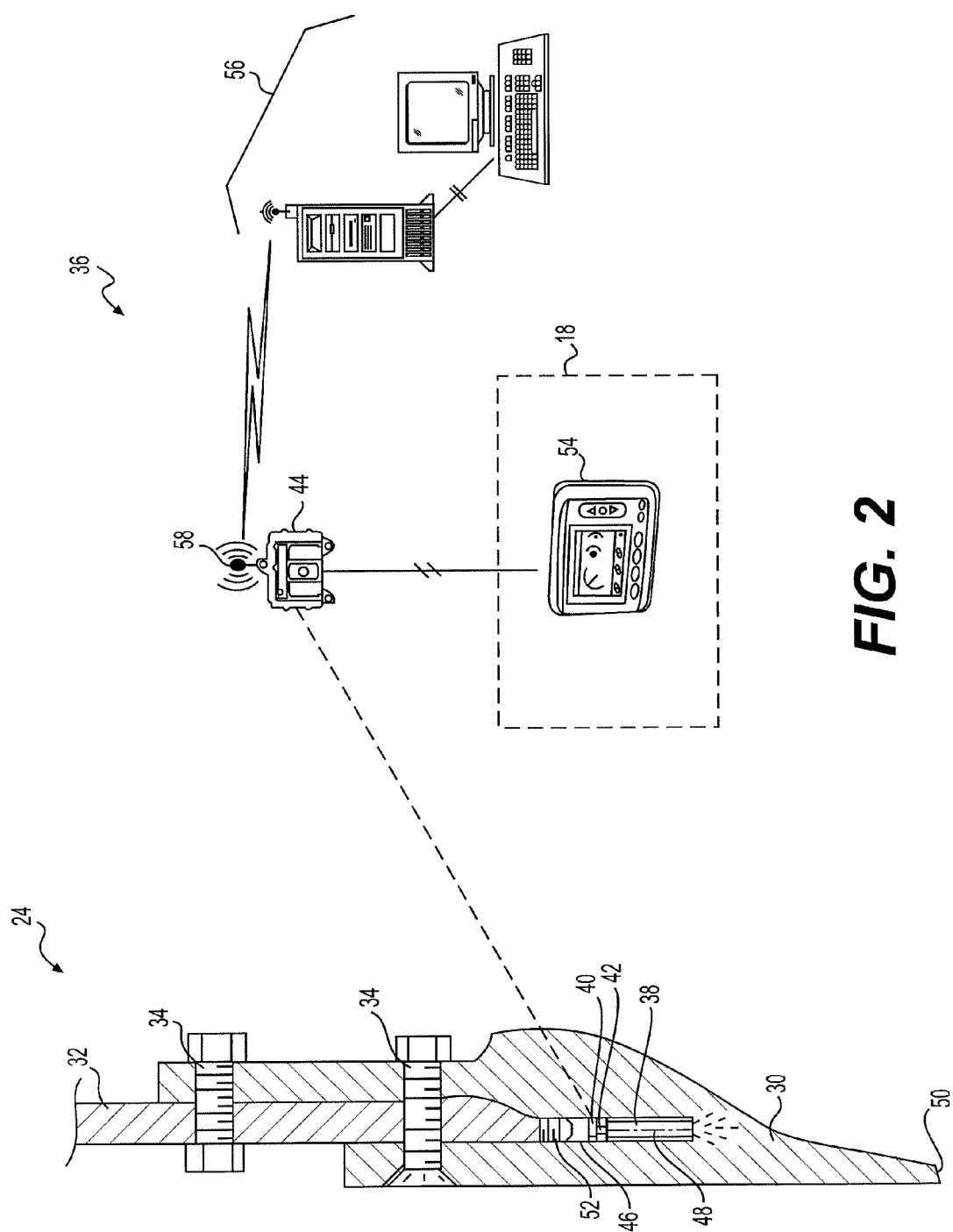
FIG. 2 is a diagrammatic illustration of an exemplary disclosed erosion monitoring system that may be used in conjunction with the machine of FIG. 1.

One or more of the ground engaging tools connected to machine 10 may be equipped with a removable cutting edge 30. Cutting edge 30 may be configured to engage a material surface and wear away throughout the life of machine 10. After cutting edge 30 has worn by a threshold amount, cutting edge 30 should be replaced to help ensure productivity and/or efficiency of machine 10. Use of cutting edge 30 may also help to reduce an amount of wear experienced by a more expensive and/or difficult-to-service base member 32 of each ground engaging tool. As shown in FIG. 2, cutting edge 30 may be removably connected to base member 32 of the corresponding ground engaging tool by way of one or more fasteners 34.

FIG. 2 illustrates an erosion monitoring system ("EMS") 36 associated with DCM 24. It should be noted, however, that EMS 36 may be equally associated with ripper assembly 26 and/or any other ground engaging tool of machine 10 having a removable cutting edge 30. As will be explained in more detail below, EMS 36 may have components that cooperate to monitor wear of cutting edge 30 and determine when cutting edge 30 should be replaced. These components may include, among other things, a sensor 38 embedded within cutting edge 30, a communication element 40 associated with sensor 38, a battery 42 configured to power sensor 38 and communication element 40, and a controller 44 mounted onboard machine 10 and in communication with sensor 38 via communication element 40.

Sensor 38 may be an ultrasonic sensor disposed within a bore 46 formed in cutting edge 30. Sensor 38 may be generally cylindrical and have a center axis 48 that is oriented at about 90° relative to a linear terminus 50 of cutting edge 30. It is contemplated that sensor 38 may have an alternative shape and/or be oriented at a different angle, if desired. As an ultrasonic sensor, sensor 38 may have a transducer that generates high-frequency sound waves within cutting edge 30. Sensor 38 may then evaluate a resulting echo that is received back by sensor 38. A time interval between sending the signal and receiving the echo is then calculated (either by sensor 38 and/or by controller 44) to determine a distance from sensor 38 to terminus 50 (i.e., the remaining wearable length of cutting edge 30). As cutting edge 30 wears, this time interval may decrease, and sensor 38 may generate a signal corresponding to the length. This signal may be directed to controller 44 for processing.

Communication element 40 may be any type of communication element known in the art capable of directing signals from sensor 38 to controller 44 wirelessly. The wireless communications may include satellite, cellular, infrared, and any other type of wireless communication. In one embodiment, communication element 40 transmits the signal acoustically and/or electrically using the material of base member 32 as a communication medium.

Battery 42 may be packaged together with sensor 38 and communication element 40 within bore 46 of cutting edge 30, and a threaded cap 52 may close off and seal an end of bore 46. It is contemplated that bore 46 may alternatively be sealed by way of a durable potting mater, if desired. Battery 42 may be configured to supply power to both of sensor 38 and communication element 40 for a finite period of time. In the disclosed embodiment, the finite period of time may be about as long as cutting edge 30 is rated for use with base member 32. In this manner, when cutting edge 30 is removed, sensor 38 and communication element 40 may be withdrawn from bore 46 and installed in the bore 46 of a replacement cutting edge 30 along with a new battery 42. Battery 42 may take any form known in the art.

Controller 44 may embody a single microprocessor or multiple microprocessors that include a means for controlling an operation of EMS 36. Numerous commercially available microprocessors can be configured to perform the functions of controller 44. It should be appreciated that controller 44 could readily be embodied in a general machine microprocessor capable of controlling numerous machine functions. Controller 44 may include a memory, a secondary storage device, a processor, and any other components for running an application and/or recording signals from sensor 38. Various other circuits may be associated with controller 44 such as power supply circuitry, signal conditioning circuitry, solenoid driver circuitry, and other types of circuitry.

One or more maps relating the signal from sensor 38 with wear values for cutting edge 30 may be stored in the memory of controller 44. Each of these maps may include a collection of data in the form of tables, graphs, and/or equations. As will be described in more detail below, controller 44 may be configured to select specific maps from available relationship maps stored in the memory of controller 44 to automatically determine and/or generate notifications regarding component wear.

The notification generated by controller 44 may be shown on a display 54 located within operator station 18. The notification may provide a visual and/or audible alert regarding a current dimension of cutting edge 30, a remaining useful life of cutting edge 30, and/or a need to replace cutting edge 30. In this manner, the operator may be able to schedule maintenance of machine 10 in advance of when cutting edge 30 is completely worn out.

In some embodiments, EMS 36 may be able to communicate with an offboard entity 56. In particular, EMS 36 may be equipped with a communication device 58 connectable with controller 44. Communication device 58 may be configured to communicate messages wirelessly between controller 44 and offboard entity 56. The wireless communications may include satellite, cellular, infrared, and any other type of wireless communication. Offboard entity 56 may be, for example, service personnel, and the communications may include messages regarding wear values, identification of worn components (e.g., particular cutting edges 30), and/or instructions for the service personnel. The instructions may be associated with directing the service personnel to provide quotes for replacement components to the owner of machine 10 and/or to schedule service of machine 10 with the owner.

INDUSTRIAL APPLICABILITY

The disclosed erosion monitoring system may be used with any machine having a ground engaging tool with a removable cutting edge. The disclosed erosion monitoring system may be capable of determining a current length of the cutting edge, an amount of useful life remaining in the cutting edge, and/or a wear rate of the cutting edge. The disclosed erosion monitoring system may also be capable of displaying notifications regarding these parameters and/or communicating the notifications to an offboard entity. The notifications may be generated continuously or, alternatively, only after a comparison with one or more threshold values indicate the need to generate the notification (e.g., only when the remaining useful life and/or current length is less than a threshold life or length).

Because sensor 38 may be assembled into an existing feature (i.e., into bore 46) of the disclosed ground engaging tools, the processes used to fabricate the ground engaging tools may not have a detrimental effect on sensor 38. In addition, because sensor 38 may not be destroyed during the use of cutting edge 30, sensor 38 may be reused, if desired. Further, sensor 38 may require little power and, hence, battery 42 may be relatively simple and inexpensive. In fact, in one example, sensor 38 may operate at a frequency of about 1/hr (i.e., generate a measurement signal about once per hour) and with this frequency of operation, battery 42 may last for about 6-9 months (or longer). This low amount of power consumption, in combination with the wireless connection between sensor 38 and controller 44, may facilitate the use of sensor 38 in harsh applications. Further, the signals generated by sensor 38 may change very little hour-to-hour and, accordingly, be highly accurate in measuring the wear rate of cutting edge 30.

It will be apparent to those skilled in the art that various modifications and variations can be made to the erosion monitoring system of the present disclosure without departing from the scope of the disclosure. Other embodiments will be apparent to those skilled in the art from consideration of the specification and practice of the erosion monitoring system disclosed herein. It is intended that the specification and examples be considered as exemplary only, with a true scope of the disclosure being indicated by the following claims and their equivalent.

What is claimed is:

1. An erosion monitoring system for a machine, comprising:
   an ultrasonic sensor embedded within a replaceable cutting edge of a ground engaging tool connectable to the machine, wherein the ultrasonic sensor is generally cylindrical and has an axis oriented at an angle of about 90° relative to a terminus of the cutting edge;
   a wireless communication element associated with the ultrasonic sensor;
   a battery associated with the ultrasonic sensor and the wireless communication element, wherein the ultrasonic sensor, the wireless communication element, and the battery are all mounted together within a bore formed inside the cutting edge; and
   a controller configured to be mounted onboard the machine in communication with the ultrasonic sensor via the wireless communication element, the controller being configured to monitor a wear rate of the cutting edge based on signals from the ultrasonic sensor, determine a length of the cutting edge, make a comparison of the length of the cutting edge to a threshold length, and selectively generate a notification based on the comparison.

2. The erosion monitoring system of claim 1, wherein the battery is configured to supply power to the ultrasonic sensor and the wireless communication element for as long as the cutting edge is rated for use on the ground engaging tool.

3. The erosion monitoring system of claim 1, wherein the bore is formed at a connection location between the cutting edge and a base member of the ground engaging tool.

4. The erosion monitoring system of claim 1, further including a threaded cap configured to engage and seal off an end of the bore.

5. The erosion monitoring system of claim 1, further including a communication device configured to transmit messages between the controller and an offboard entity.

6. The erosion monitoring system of claim 1, wherein the notification is indicative of an estimated useful life of the cutting edge.

7. The erosion monitoring system of claim 6, further including a display located onboard the machine, wherein the notification is shown on the display.

8. The erosion monitoring system of claim 6, wherein the notification is transmitted to an offboard entity.

9. The erosion monitoring system of claim 1, wherein the communication element facilitates communication of signals between the ultrasonic sensor and the controller via a base material of the ground engaging tool.

10. A ground engaging tool, comprising:
    a base member;
    a cutting edge removably connected to the base member, the cutting edge having a bore formed therein;
    an ultrasonic sensor disposed within the bore and configured to generate a signal indicative of a length of the cutting edge, wherein the ultrasonic sensor is generally cylindrical and has an axis oriented at an angle of about 90° relative to a terminus of the cutting edge;
    a battery associated with the ultrasonic sensor, wherein the battery is mounted together with the ultrasonic sensor inside the bore; and
    a controller in communication with the ultrasonic sensor, the controller being configured to determine a length of the cutting edge, make a comparison of the length of the cutting edge to a threshold length, and selectively generate a notification based on the comparison.

11. The ground engaging tool of claim 10, wherein the bore is formed at a connection location between the cutting edge and the base member.

12. The ground engaging tool of claim 10, further including a threaded cap configured to engage and seal off an end of the bore.

13. A machine, comprising:
    a frame;
    an engine supported by the frame;
    a traction device configured to support the frame and be driven by the engine;
    a ground engaging tool connected to the frame and having a base member;
    a cutting edge removably connected to the base member of the ground engaging tool, the cutting edge having a bore formed therein at a connection location between the cutting edge and the base member;
    an ultrasonic sensor embedded within the bore of the cutting edge and having an axis oriented at about 90° relative to a terminus of the cutting edge;
    a wireless communication element associated with the ultrasonic sensor;
    a battery configured to power the ultrasonic sensor and the wireless communication element, wherein the battery is embedded with the ultrasonic sensor within the bore of the cutting edge; and
    a controller mounted onboard the machine in communication with the ultrasonic sensor via the wireless communication element, the controller being configured to:
    determine a length of the cutting edge;
    make a comparison of the length of the cutting edge to a threshold length; and
    selectively generate a notification based on the comparison.

* * * * *